US011949666B2

(12) United States Patent
Croall

(10) Patent No.: US 11,949,666 B2
(45) Date of Patent: Apr. 2, 2024

(54) CHROMOSOMAL IDENTIFICATION

(71) Applicant: Paul Andrew Croall, Buckinghamshire (GB)

(72) Inventor: Paul Andrew Croall, Buckinghamshire (GB)

(*) Notice: Subject to any disclaimer, the term of this patent is extended or adjusted under 35 U.S.C. 154(b) by 512 days.

(21) Appl. No.: 17/250,612

(22) PCT Filed: Aug. 12, 2019

(86) PCT No.: PCT/GB2019/052268
§ 371 (c)(1),
(2) Date: Feb. 10, 2021

(87) PCT Pub. No.: WO2020/030937
PCT Pub. Date: Feb. 13, 2020

(65) Prior Publication Data
US 2021/0320905 A1  Oct. 14, 2021

(30) Foreign Application Priority Data
Aug. 10, 2018 (GB) .................... 1813130

(51) Int. Cl.
*H04L 27/06* (2006.01)
*G16B 30/10* (2019.01)
(Continued)

(52) U.S. Cl.
CPC .......... *H04L 63/0442* (2013.01); *G16B 30/10* (2019.02); *H04L 9/0866* (2013.01);
(Continued)

(58) Field of Classification Search
CPC . H04L 63/0442; H04L 9/0866; H04L 9/3236; H04L 9/3231; H04L 63/0861; G16B 30/10; G06Q 50/01; G06Q 2220/10
See application file for complete search history.

(56) References Cited

U.S. PATENT DOCUMENTS 9,942,206 B1 * 4/2018 Miller ................. H04L 63/0428
2014/0289536 A1 * 9/2014 MacCarthy ......... G06F 21/6245
713/189
(Continued)

FOREIGN PATENT DOCUMENTS

CN 106796628 A * 5/2017 ............. G06F 21/32
WO WO-2013067542 A1 * 5/2013 ......... G01N 33/6803

OTHER PUBLICATIONS

Mandge et al., "A DNA encryption technique based on matrix manipulation and secure key generation scheme", 2013 International Conference on Information Communication and Embedded Systems (ICICES), Feb. 21-22, 2013).*

(Continued)

*Primary Examiner* — Morshed Mehedi
(74) *Attorney, Agent, or Firm* — Boisbrun Hofman, PLLC

(57) ABSTRACT

The present invention relates to a method, apparatus, and system for communication with a user's family members using the DNA of the user without making the DNA profile public. According to a first aspect, there is provided a computer implemented method of locating one or more members of a familial network, comprising the steps of: generating one or more encryption keys derived from a first genomic sequence; encrypting a message using the or each encryption key to form an encrypted message; sending the encrypted message to one or more remote devices wherein decrypting the encrypted message at the one or more remote devices uses one or more encryption keys derived from a second genomic sequence; and receiving a confirmation regarding whether the decryption of the encrypted message was successful by any of the one or more remote devices.

20 Claims, 8 Drawing Sheets

(51) Int. Cl.
H04L 9/08 (2006.01)
H04L 9/32 (2006.01)
H04L 9/40 (2022.01)
G06Q 50/00 (2012.01)

(52) U.S. Cl.
CPC ........... H04L 9/3236 (2013.01); *G06Q 50/01* (2013.01); *G06Q 2220/10* (2013.01)

(56) References Cited

U.S. PATENT DOCUMENTS

2015/0112884 A1* 4/2015 Ostrovsky .............. G16B 30/10
705/325
2018/0108019 A1* 4/2018 Schneider .......... G06Q 20/3821

OTHER PUBLICATIONS

PCT/GB2019/052268 International Preliminary Report on Patentability dated Jul. 28, 2020, 15 pages.
Farhad Hormozdiari et al., "Privacy preserving protocol for detecting genetic relatives using rare variants", Bioinformatics, vol. 30, Issue 12, Jun. 15, 2014, pp. i204-i211.
Application No. 2019320572, Australian Examination Report dated Jun. 12, 2021, 7 pages.

* cited by examiner

CHROMOSOMAL IDENTIFICATION

FIELD

The present invention relates to the identification of and communication with genetically similar people. More particularly, the present invention relates to a method, apparatus, and system for communication with a user's family members using the DNA of the user without making the DNA profile public.

BACKGROUND

The deoxyribonucleic acid (DNA) profile of every human can act as a very specific marker identifying that particular human. Some humans, for example those closely related to each other biologically, can share a greater proportion of their DNA with such family members compared to more remote families. Therefore, by comparing the DNA profile of two or more people, one can provide an accurate measure of biologically familial closeness between those people.

It can be very difficult to find family members, especially deceased former family members, when lacking in physical information such as an approximate location or a given name.

SUMMARY OF INVENTION

Aspects and/or embodiments seek to provide a method, apparatus, and system for communication with a user's family members using the DNA of the user without making the DNA profile public.

According to a first aspect, there is provided a computer implemented method of locating one or more members of a familial network, comprising the steps of: generating one or more encryption keys derived from a first genomic sequence; encrypting a message using the or each encryption key to form an encrypted message; sending the encrypted message to one or more remote devices wherein decrypting the encrypted message at the one or more remote devices uses one or more encryption keys derived from a second genomic sequence; and receiving a confirmation regarding whether the decryption of the encrypted message was successful by any of the one or more remote devices.

According to a further aspect, there is provided a computer implemented method of locating one or more members of a familial network, comprising the steps of: receiving an input comprising a first genomic sequence; generating one or more encryption keys based on the input; encrypting a message using the or each encryption key to form an encrypted message; sending the encrypted message to one or more remote devices wherein decrypting the encrypted message at the one or more remote devices uses one or more further genomic sequences; and receiving a confirmation regarding whether the decryption of the encrypted message was successful by any of the one or more remote devices using the one or more further genomic sequences.

Optionally, the method disclosed herein further comprises the steps of: receiving an input comprising a first genomic sequence; and generating one or more encryption keys based on the input. Optionally, the step of decrypting the encrypted message at the one or more remote devices uses one or more encryption keys derived from one or more further genomic sequences.

The arrangement disclosed herein, also referred to as the chromosomal identification arrangement, provides the ability to communicate with potentially lost family members, using the DNA of a sender without making any DNA public. The sender (or "user") may comprise a person who is entering their DNA into the chromosomal identification arrangement in order to make use of the arrangement provided herein. For example, a lost family member may be identified and reconnected with. As genomic data may be considered private, it is important to attempt to very carefully limit who can access the data. To this end, a sequenced genome comprising or derived from the DNA of the user may be used to create a genetic address. A user can have prepared for them a chromosomal identification arrangement to encrypt a message. The metric used for encryption is encoded in the genome or in one or more of the properties of the genome. Specifically, in one embodiment properties of the genome can comprise properties of the mitochondria, and X and Y chromosomes. The message is not the sequence itself as this is intended to be kept private, but is some other data (e.g. a message) encrypted using an encryption key derived from the genomic sequence.

Optionally, one or more of the encryption keys comprises: a first encryption key for a verbatim encryption algorithm, and a second encryption key for a unique encryption algorithm. Optionally, the first encryption key is used in relation to: one or more mitochondria; a first X chromosome; and a second X chromosome or a Y chromosome, to form three verbatim algorithmically generated ciphers in relation to the first genomic sequence. Optionally, the second encryption key is used to encrypt the message using a combination of chromosomes 1 through 22 comprised in the first genomic sequence. Optionally, the step of sending the encrypted message is performed using one or more outputs derived from the first genomic sequence.

The verbatim cryptography used as part of the verbatim encryption algorithm takes advantage of the fact that these three chromosomes can be passed from parent to offspring, with certain provisos, verbatim. Chromosomes 1 through 22 together, with rare exceptions, are conventionally accepted as being unique to each individual. Encryption can hence be performed using the chromosomes which tend to be unique to each individual but taking into account the fact that portions of the abovementioned chromosomes may be shared with relatives.

Optionally, the successful decryption of the encrypted message is indicative of a predetermined level of familial closeness. Optionally, the first and/or one or more further genomic sequences comprises at least a portion of a genome sequence. Optionally, the first and/or second genomic sequences comprises at least a portion of a genome sequence When considering that portions of the abovementioned chromosomes may be shared with relatives, a successful decryption of the encrypted message must mean that the data from the DNA of the user decrypting the message comprises at least a portion in common with the DNA of the user encrypting the message.

Optionally, a genomic sequence comprises four bases comprising one or more of: guanine (G), cytosine (C), adenine (A), thymine (T), and/or uracil (U).

These bases are used as constituent parts of a conventional genomic sequence, as they are the bases which are used to constitute DNA.

Optionally, the four bases are mapped to a binary sequence. Optionally, the binary sequence comprises two forms: pressed and/or unpressed. Optionally, the input comprises the number of one or more of the four bases.

Each chromosome may be held in a binary form, 4 bits per base 4 digit, and cryptographic and bitwise operations can be carried out upon them for use as keys. Such use may comprise pressing them into a form that can be viewed as 2 bits per base 4 digit. This structure avoids excessive paging of a not insignificant amount of data given an entire human genome, thereby reducing the runtime RAM consumption of sequenced chromosomes. This process may be referred to as a product of DNA, or ProDNA.

Optionally, the decryption of the encrypted message is successful only if a predetermined proportion of the first genomic sequence corresponds to the one or more further genomic sequences. Optionally, the predetermined proportion reflects the level of familial relationship between an owner of the first genomic sequence and an owner of the one or more further genomic sequences. Optionally, the decryption of the encrypted message is successful only if a predetermined proportion of the first genomic sequence corresponds to the second genomic sequence. Optionally, the predetermined proportion reflects the level of familial relationship between an owner of the first genomic sequence and an owner of the second genomic sequence.

If two individuals share more than a predetermined proportion of their genomic sequences, it is likely to be indicative of the biological closeness between those two individuals. It may be advantageous to contact only relatives, otherwise a large number of spurious messages will be sent and the accuracy of finding one's relatives reduced.

Two concepts will now be introduced to facilitate understanding of the following description and the embodiments described later. The two concepts are "volume" and "loudness". In this context, "volume" does not refer to a quantity of DNA, it relates to a preference with regards to the intended audience for a given communication. The scale on which volume is measured for the purposes of this description can be referred to as "loudness". The louder the volume, the further afield it can be heard, in terms of genetic distance. By setting the volume as one might set the volume on a music system to loud or quiet or anywhere in between, it is determined who can hear the message (i.e. the intended audience for a given communication). The loudness determines how far away a user can be genetically from the sender (i.e. genetic distance) and still "hear" their message. Whereas on a music system volume typically relates to a single scale, here there may be multiple scales or properties which are adjusted in a balanced fashion, in line with the volume setting. The setting of a volume may be considered as a simpler means for strangers to agree a complex set of calibration details. Instead of considering such variables they may simply set a volume.

The following two observations may be made by a user in relation to setting the volume:

1. When sending a message, the "louder" the volume is set, the more people their message will reach as even more distant relatives are able to successfully decrypt the message; and vice versa, and
2. When receiving a message, the louder the volume is set, the more messages will be received from even more distant relatives, and vice versa.

In principle, identical twin siblings will have identical DNA. Even a single base-pair difference, perhaps introduced by a sequencing error, may be adequate to distinguish them but such an error may not occur. In such an exemplary scenario, each identical sibling may use the method disclosed herein to find the same individual. Despite the genetic similarity, one difference may be that the two will not have had their genome sequenced at exactly the same moment. Therefore a sufficiently accurate timestamp from each sequence file may be used to distinguish each sibling. This mechanism of distinguishing identical siblings may be a non-ideal solution when compared to a conventional case without an identical sibling. However, it may still be important to provide such a distinguishing means. It is appreciated that this particular method of distinguishing identical siblings may represent one of several options which could be adopted, and other means may be apparent to a skilled person.

Optionally, the step of sending the encrypted message comprises forming an array of three by four integers and a unique individual hashed integer identifier. Optionally, the unique individual hashed integer is a hash of an entire genome sequence. Optionally, the unique individual hashed integer further comprises a superimposition of a timestamp of the sequencing date.

DNA-related information, such as a genomic sequence, can be extremely personal information that a user may not wish to share widely. Therefore, it is advantageous if the exact nature of such information can remain encrypted or otherwise encoded even when used to identify relatives. A user may not fully trust said relatives and hence may wish to keep such personal information private to themselves only.

Optionally, the step of encrypting the message comprises the use of a binary large object of prime sized words (BoPSW).

As detailed herein, BoPSW can provide a secure and computationally-efficient means of encryption in relation to the data used in the chromosomal identification arrangement.

Optionally, the or each of the one or more nodes of the distributed network of nodes is only operable to send the encrypted message only the first time that the encrypted message is received by the or each node.

In one embodiment, a node may only relay a message the first time it receives it, and will not allow the receipt to happen a second time, although if it receives a fresh translation of the message then that may also be relayed. Having grouped together all of those messages for relaying the node comprises the details of an enlarged potential family. However the family size will be restricted by one or more of the volume calibration details of the message being relayed. The above arrangement may be bootstrapped by, before it has received any messages, each node having a pre-configured gateway, or preferably two, of other nodes. Should the owner of a node wish to send a message before the node has ever received a message, the message will be forwarded to the gateway as in at least one embodiment there is nowhere else to forward it. Once a node has sent a message its address becomes known by the network as described above and from that point forward it may receive targeted messages.

Optionally, the or each node of the distributed network has an associated user.

A user may be linked to a particular node in order to identify that user.

Optionally, the arrangement disclosed herein further comprises the step of: outputting a measure of genetic distance between the first genomic sequence and the one or more further genomic sequences. Optionally, the arrangement disclosed herein further comprises the step of: outputting a measure of genetic distance between the first genomic sequence and the second genomic sequence. Optionally, the measure of genetic distance is determined using a DNA address.

A user may only wish to correspond with other users within a particular biological range. Therefore, it may be advantageous to provide such a measure as can be understood by a user.

Optionally, the encrypted message is stored for a portion of time on a remote server. Optionally, the decryption of the encrypted message following the step of sending the encrypted message takes place after a time delay.

Users of the chromosomal identification arrangement may be physically based across large distances and hence be a part of different networks and/or servers. However, they may still wish to use the arrangement alongside their physically distant relations.

According to a further aspect, there is provided a familial network location apparatus, comprising: a processor operable to: receive an input comprising a first genomic sequence; generate one or more encryption keys based on the input; encrypt a message using the or each encryption key to form an encrypted message; send the encrypted message to one or more devices wherein decrypting the encrypted message at the one or more devices uses one or more further genomic sequences; and receive a confirmation regarding whether the decryption of the encrypted message was successful by any of the one or more remote devices using the one or more further genomic sequences.

According to a further aspect there is provided a familial network location apparatus, comprising: a processor operable to: generate one or more encryption keys derived from a first genomic sequence; encrypt a message using the or each encryption key to form an encrypted message; send the encrypted message to one or more devices wherein decrypting the encrypted message at the one or more devices uses one or more encryption keys derived from a second genomic sequence; and receive a confirmation regarding whether the decryption of the encrypted message was successful by any of the one or more remote devices.

According to a further aspect there is provided a system to locate one or more members of a familial network, comprising: a processor operable to: receive an input comprising a first genomic sequence; generate one or more encryption keys based on the input; encrypt a message using the or each encryption key to form an encrypted message; send the encrypted message to one or more devices wherein decrypting the encrypted message at the one or more devices uses one or more further genomic sequences; and receive a confirmation regarding whether the decryption of the encrypted message was successful by any of the one or more remote devices using the one or more further genomic sequences.

According to a further aspect there is provided a system to locate one or more members of a familial network, comprising: a processor operable to: generate one or more encryption keys derived from a first genomic sequence; encrypt a message using the or each encryption key to form an encrypted message; send the encrypted message to one or more devices wherein decrypting the encrypted message at the one or more devices uses one or more encryption keys derived from a second genomic sequence; and receive a confirmation regarding whether the decryption of the encrypted message was successful by any of the one or more remote devices.

The apparatus and system allow for the method of chromosomal identification and associated message transmission to be performed.

BRIEF DESCRIPTION OF DRAWINGS

Embodiments will now be described, by way of example only and with reference to the accompanying drawings having like-reference numerals, in which.

SPECIFIC DESCRIPTION

Figure 1:
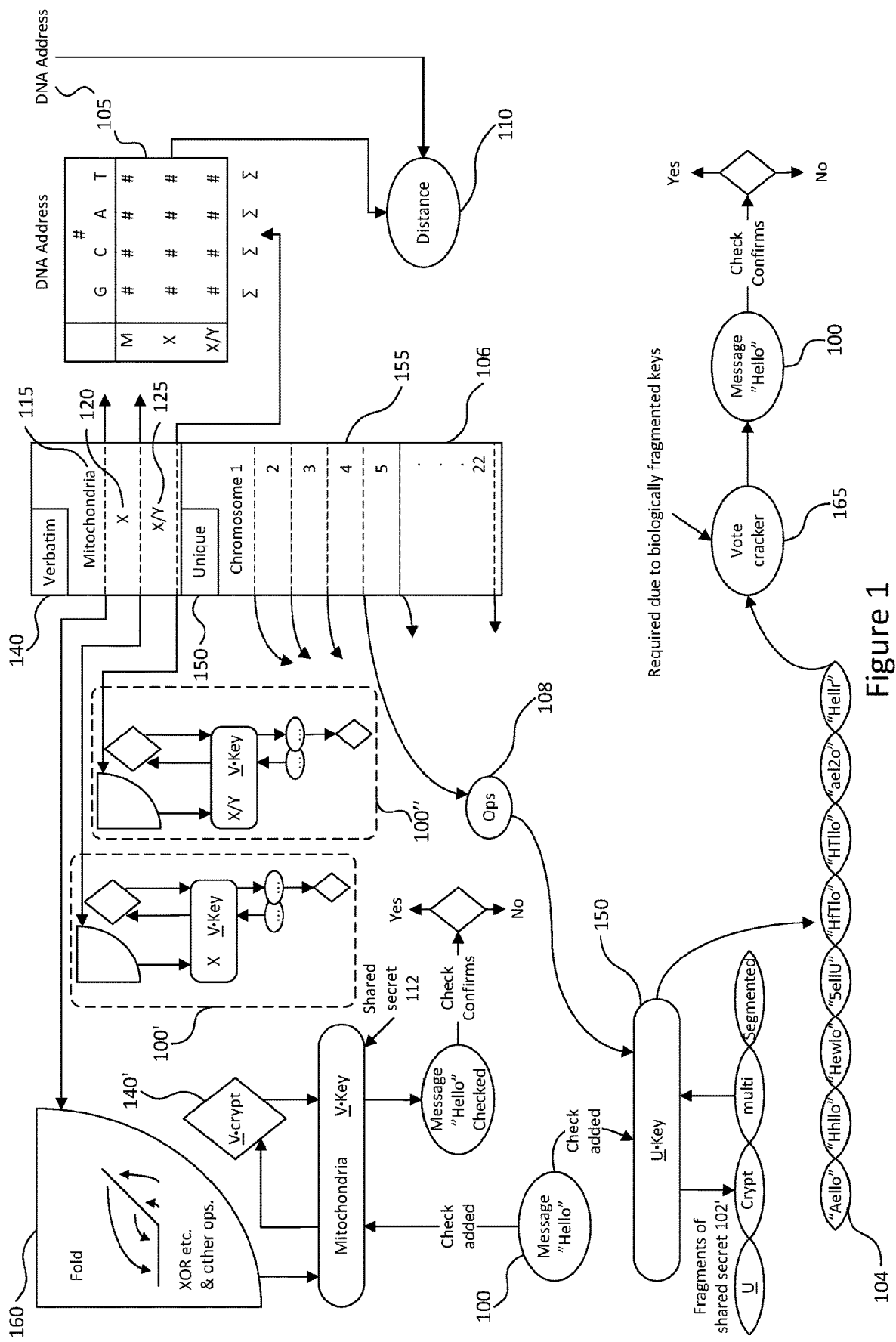
FIG. 1 shows a high-level schematic overview of the arrangement as disclosed herein.

Referring to FIG. 1, a first embodiment will now be described. A sequenced genome 106 comprising the DNA of the user is used to create a genetic address 105 for routing purposes. The user then uses the chromosomal identification arrangement to encrypt a message 100 into an encrypted message 104, 140' that may then be sent to potentially lost family members, where they may not even know the recipient's name, approximate whereabouts, nor any other relevant tracking information. The key 140, 150 used for encryption is derived 108 from the genome or from one or more of the properties of the genome. Specifically, in one embodiment, properties of the genome include properties of the mitochondria, and X and Y chromosomes. Many users will have identical copies of their close relatives' matching mitochondria, and/or X and/or Y chromosomes.

A human has three key genetic roots. For men, each of those roots may be considered as planted in a land (a term which may be used interchangeably with "domain" or "property") of its own type, containing only that type of root. Women have one of the roots shared with one of the male roots, two of the roots shared with another of the male roots, but don't touch the third land. In this example, the roots represent the mitochondria chromosome 115, the X chromosome (or chromosomes) 120, and the Y chromosome 125.

Each individual has their three roots in three specific locations within the land in question. In each case the location can be identified using four dimensional coordinates. A coordinate can be defined as $\Sigma G, \Sigma C, \Sigma A, \Sigma T$ where $\Sigma$ is used to indicate the number of that particular base within the chromosome in question where G, C, A and T refer to guanine, cytosine, adenine and thymine respectively. This calculation may be summarised in table 105.

It can be assumed that a particular three sets of coordinates are not shared with most people. Such people they are not shared with, by a particular definition of close relative, are not a close biological relative of the user from whom the DNA was taken to generate those particular three sets of coordinates. The few who do share at least one of their genetic locations with the user have a greater chance of being a close biological relative. If a person is only a mutation or two away from the user's genetic location there is a much greater likelihood that a close biological relative has been found.

Different messages 100' and 100" (or as many as required) may be broadcast using this arrangement, but with different settings to allow for a different intended audience for example. In a specific example, message 101' may be intended for only very close family members and the encryption settings for this message 101' would require the message to be decrypted by those only with very similar genetic sequences as the sender, while message 101" may be intended for a more distantly related audience of genetic relations as the sender.

Figure 2:
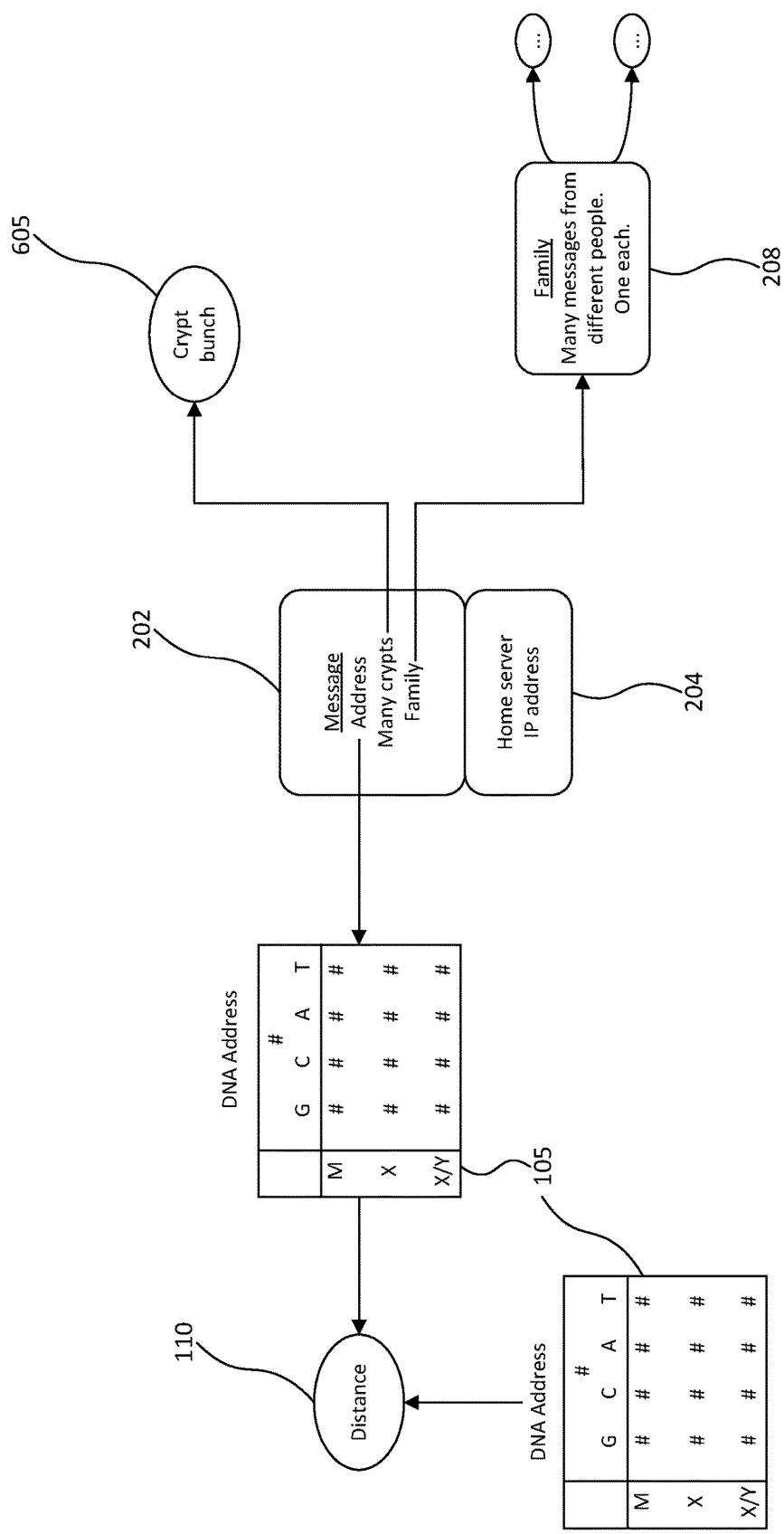
FIG. 2 shows an example of a distance calculation between family members.

By eliminating most people who are not genetically close to a user, a far smaller pool of people remain who are more likely to be closely genetically related to you and hence produce a measure of familial distance 110. Using the coordinate system above a less computationally expensive way of connecting those who wish to be connected may be provided. An example of a measuring process for genetic closeness is represented in FIG. 2.

It is appreciated that there is desire to maintain privacy of DNA. DNA can represent extremely personal information which many users may not wish to share. Therefore, when a potential biological relative is found, messages are able to be exchanged and encrypted using each of their genomes as a part of their respective keys. Only a matching genome will make decryption possible, thereby helping to eliminate any false positives. This method provides an alternative to providing strangers, who may end up being unrelated, personal details such as a genomic sequence.

The chromosomal identification arrangement is operable to deduce from an individual's genome a DNA address which may be partially represented within the table 105:

|     | G | C | A | T |
| --- | --- | --- | --- | --- |
| M   | Σ | Σ | Σ | Σ |
| X   | Σ | Σ | Σ | Σ |
| X/Y | Σ | Σ | Σ | Σ |

Σ represents how many of this base are in the chromosome when multiplied by 12.

Sometimes there is uncertainty as to which base is represented in a particular genome sequence. If the base is known to within a predetermined degree of certainty, then each the number of each known base counts as 12. If a base is not known to within a predetermined degree of certainty, and could be any of the 4 bases, then each one counts as 3. If a base could be any of a specific 3 bases only, then each one of those 3 counts as 4 and the remaining one is zero. If the unknown base could be any of a specific 2 bases only, then each one of those 2 counts as 6 and the other 2 are zero.

For the purposes of simplified calculation, it is considered that there are typically 16,569 base pairs in the human mitochondrial DNA, approximately 58,000,000 base pairs in the Y chromosome and approximately 155,000,000 base pairs in the X chromosome. Any given base must be of the form G, C, A or T. Any two people picked at random from a population are likely to have a different number or quantity of any given base pair in each of their mitochondria, X and Y chromosomes. Multiplying out the possible combinations of quantities of base pairs generates a result which is many orders of magnitude larger than the current human population. A bell-curve distribution is produced which can be used advantageously. Instead of every person having their own unique slot in the distribution, closely related people will be closer together on the bell-curve and so closely related people will have the same slot in the distribution generated. Therefore, the results can be arranged in an ordered queue and any given individual's close relatives can be considered as in the same part of that queue.

Twelve separate such queues are established:
1) The number of "G"s in the mitochondrial chromosome;
2) The number of "C"s in the mitochondrial chromosome;
3) The number of "A"s in the mitochondrial chromosome;
4) The number of "T"s in the mitochondrial chromosome;
5) The number of "G"s in the X chromosome;
6) The number of "C"s in the X chromosome;
7) The number of "A"s in the X chromosome;
8) The number of "T"s in the X chromosome;
9) The number of "G"s in the Y chromosome;
10) The number of "C"s in the Y chromosome;
11) The number of "A"s in the Y chromosome; and
12) The number of "T"s in the Y chromosome.

Whereas biological females have two X chromosomes, males have one X and one Y chromosome. This results in females having two slots in the X queues, but do not feature in the Y queue at all. A close relative will match in at least four of the queues, because they will have a chromosome in common.

Each queue may comprise over ten thousand slots. Given an individual, on any given queue, a very high proportion of people are likely to be in a different slot. Most queues must have orders of magnitude more slots and so this proportion gets even higher. This means that an individual can only match with up to 0.01% of the human population. That number may be currently estimated at approximately 760,000 people.

When looking at the Y chromosome only, these queues will be orders of magnitude larger than 10,000. The Y chromosome is three orders of magnitude longer than the mitochondria. Those three orders of magnitude can be used to reduce the above number of 760,000 people to 760 people, globally. The X chromosome is even longer than the Y chromosome. However, 760 people is still a greater number of unknown people than a potential user may wish to inform of their personal and potentially very private DNA sequence.

A computer architecture may be used to carry out the arrangement disclosed herein in the form of a sparse array implemented using a tree. This offers the benefits of an array, plus those of a tree. The tree implementation of a sparse array may be used in conjunction with DNA addresses to associate the most closely related individuals to each other. ProDNA implements a binary representation of a chromosome, with the ability to perform operation on a ProDNA or between a plurality of ProDNA, rendering a new ProDNA without needing to consume additional memory beyond the initial base load and a portion of metadata which may be comparatively small compared to the initial base load.

Such operations are useful for cryptography. Operations may comprise one or more of: XORing, folding and pressing as represented in step 160. Classically, at load time, a ProDNA represents the hexadecimal form of the sequence.

A "PressedProDNA" is the result of pressing a ProDNA. Verbatim cryptography, as described herein, may require a higher quality sequencing and hence benefits from pressing the chromosome first. By contrast, unique cryptography can be used alongside a lower quality sequence with less difficultly especially when the ProDNA has not had the questions pressed out of it.

A sequencing process can result in some uncertainty as to exactly what was read. Unpressed ProDNAs may represent the uncertainty. Such uncertainty may comprise the question as to whether a given base pair is actually, for example, G or T. It may be known that it is not A or C, but there remains a question as to whether it is G or T. Converting an unpressed ProDNA into a pressed ProDNA requires a decision to be made about that uncertainty question. Under such circumstances the decision may be based on probability. However a more accurate option may be to use a higher quality sequencing mechanism, eliminating the need to use probabilities. High quality sequences may be obtained by repeating the sequencing process until clarity emerges.

A "ProDNAFold" is the result of folding a ProDNA, without claiming another significant quantity of memory. This process may be helpful in key production. A "ProDNAXORed" is the result of XORing a ProDNA, without claiming another significant quantity of memory. This process may also be relevant to key production.

Figure 3:
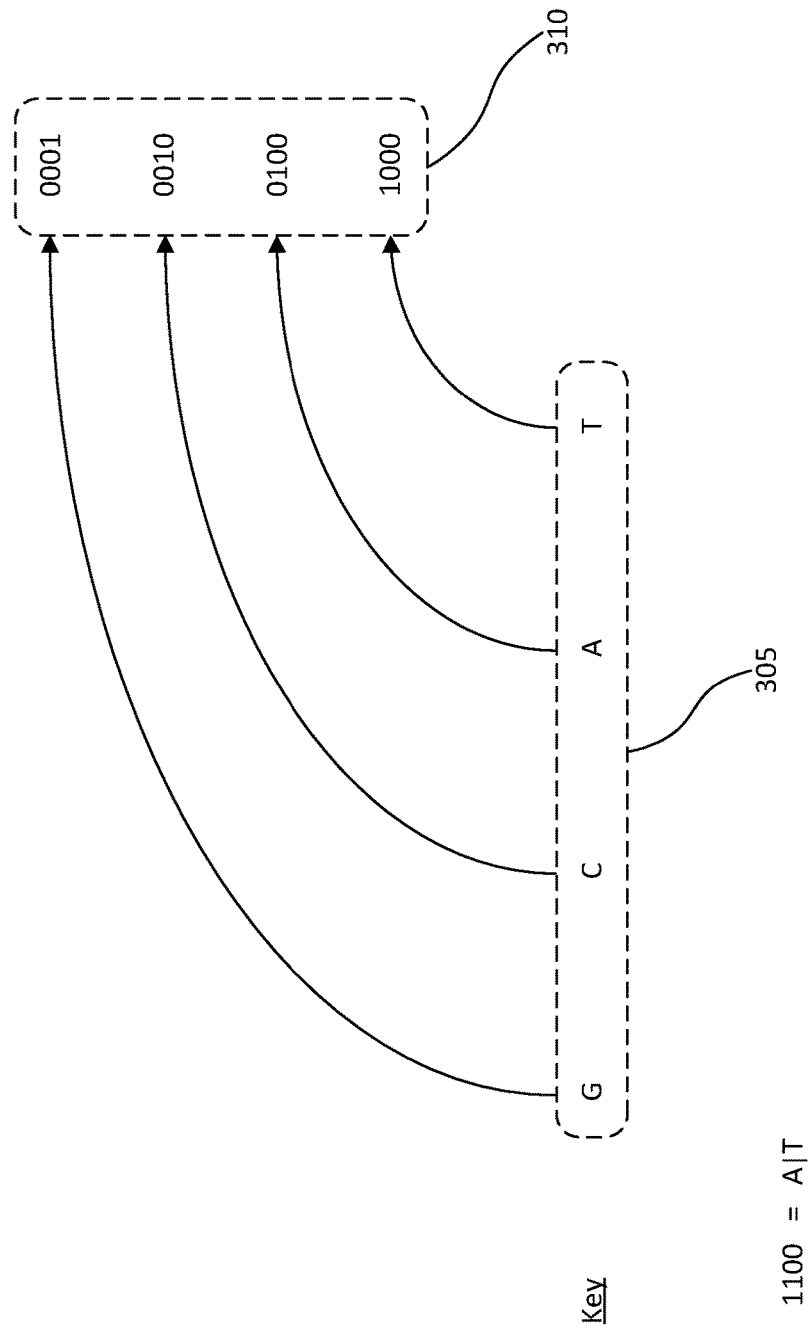
FIG. 3 shows an exemplary representation of DNA constituent parts in a binary form.

As shown in FIG. 3, base pairs may be mapped into four bit binary, leaving redundancy to manage uncertainty when in unpacked form. Computers conventionally use a binary (base 2) system of measurement when performing calculations. DNA may be considered as base 4, 310, as there are 4 constituent forms, namely G, C, A and T, 305. Mapping from base 4 to binary can be performed without excessive computational strain as each base 4 digit takes up two binary digits, unless there is uncertainty as to exactly which base 4 digit is being used. Such uncertainty can be addressed in part by treating the DNA as hexadecimal (base 16), rather than base 4, thereby mapping to 4 bits per hexadecimal digit.

For production of DNA Address including encryption and decryption, the chromosomes require morphing into a repeatable consistent binary form. These representations give a consistent binary form.

V encryption, which uses base four, may offer the greatest confidence when a match is made but is vulnerable to uncertainty caused by low quality sequencing. Therefore optimal cryptographic purposes may require the use of pressed ProDNA. It is noted that using unpressed ProDNA for V encryption may be ineffective as the cases where the unpressed benefit cuts in are also the cases where V encryption will fail to decrypt anyway. U encryption, which uses base sixteen (also referred to as hexadecimal), offers a wider spectrum or distance of matches, and may be considered more resilient to uncertainty.

The uncertainty may be absorbed in the larger problem of U keys only being partial matches for each other. V keys, by definition, need to be substantially perfect matches for each other.

While the uncertainty can be statistically dealt with for routing purposes, it is problematic when attempting to use such "dirty" data as a shared secret key 112 (in at least one embodiment including the V key and/or mitochondria). However unique key or voting cryptography naturally overcomes these problems.

Similarities are noted between the core dump of a computer and a chromosome. Both can be viewed as a series of numbers. Both programmatically define algorithms. In the case of human chromosomes, the programs for building a human being. A core dump can occur when the computer crashes. It may comprise a mess of numbers with hidden meanings, as well as also number sequences which are no longer used or were never used but make for evidence of interest. A chromosome may also be understood as a mess of numbers with hidden meanings, as well as number sequences which are no longer used or some were never used but make for evidence of interest.

Both the core dump of a computer and a chromosome can have been inadvertently impacted, usually with no or minimal adverse consequences, but in the context of a chromosome, very rarely with positive consequences. This is understood to be a key driver within biological evolution. In the computer context, the positive consequences tend to be by design, whereas evolution depends upon a significant attrition rate.

Figure 4:
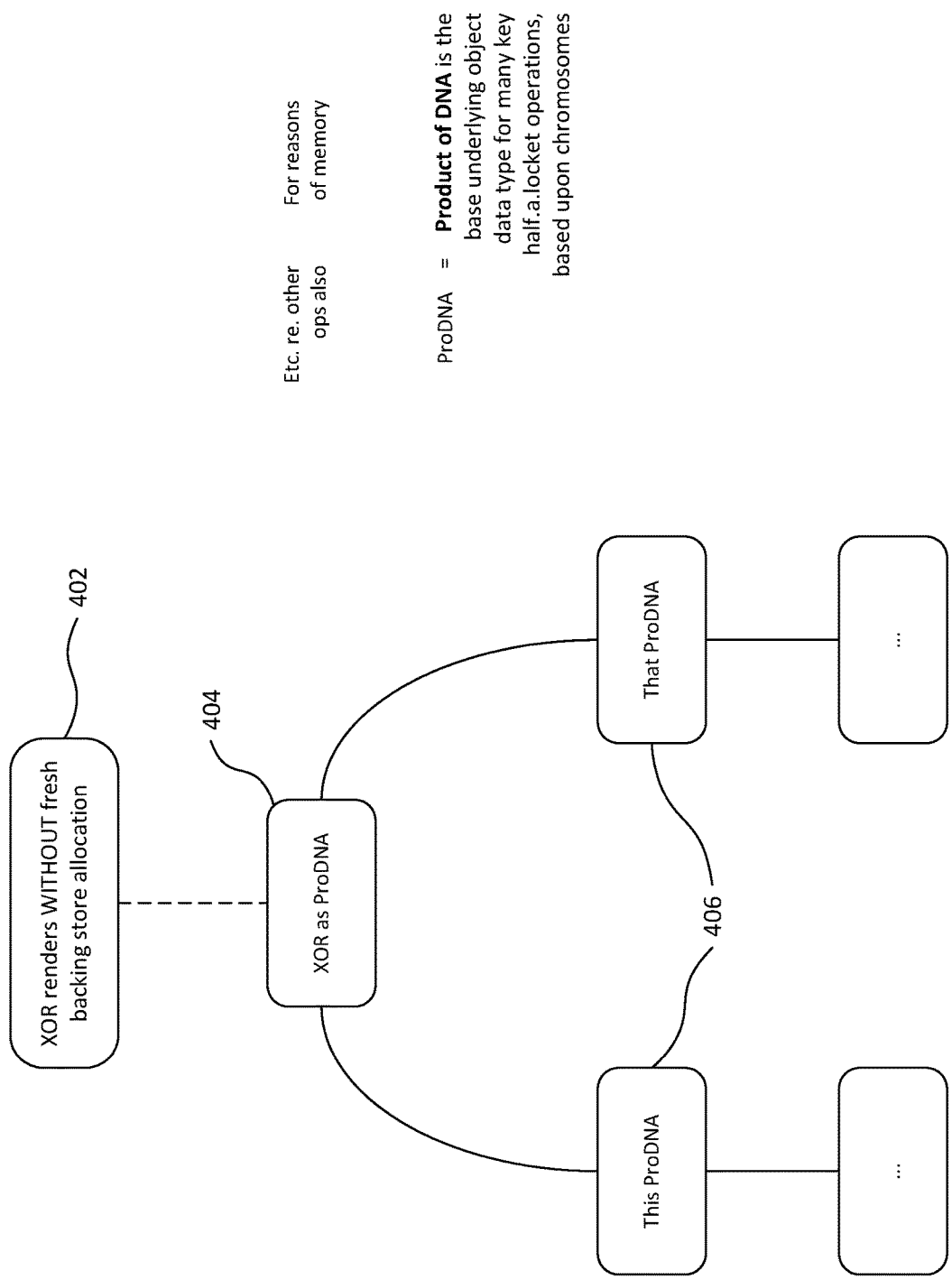
FIG. 4 shows an exemplary calculation of the product of DNA.

The ProDNA process is operable to reduce computational expense when analysing a sequenced chromosome as described herein, is shown in FIG. 4. An unpressed ProDNA may, for example, represent G in binary as 0001. It will represent C as 0010, A as 0100, and T as 1000. A pressed ProDNA may represent G as 00, C as 01, A as 10 and T as 11. In this example, the difference being that unpressed takes up twice as many binary digits as the pressed corresponding versions. Correspondingly, an unpressed ProDNA would take 1001 as meaning that there is a question as to whether that particular base-pair is actually G or T.

FIG. 4 shows two ProDNAs 406, each of which are backed by a large memory store. An XOR operation 404 is carried out upon then, resulting in a third ProDNA 402. This third ProDNA is not a duplication of the memory requirements of the original two, as there is just metadata connecting them. Actual computations are delayed to a "just in time" (JIT) stage. This may provide a fine balance of computational and memory demand.

To improve the reliability of the chromosomal identification arrangement it can be important to distinguish any false positives from the true positives. In one embodiment this is performed by sending an encrypted message using the sender's genome as the key. The receiver must have sequences of DNA in common with the sender to decrypt the message. The message will be unintelligible to others. By sending the message, the chromosomal identification arrangement is operable to detect the required information to relay messages back to the sender from other family members, wherever they were sent from. Messages from other family members may then be delivered back to the sender, and hence the family members are placed back in communication with each other. Individuals own confidential genome sequence is protected by the fact that the DNA Address itself is a form of hash of the individual's genome sequence, rather than the sequence itself. This safety feature may introduce a risk of false positives. When a false positive occurs in this way, it may be referred to as a super-state match. Super-state matches are addressed by not presuming an actual relationship until a message is successfully encrypted using a verbatim 140 crypt 140' or unique 150 crypt based on the DNA sequence of one party, and decrypted using the DNA sequence of the other.

In at least one embodiment, the crypt 605 is created in a multi-segmented form 620. The entire message is encrypted using a portion of the key and the result stored in the first segment. Then the entire message is encrypted again using a different portion of the key and the result stored in a different segment. This process may be repeated a plurality of times.

Encryption occurs by exclusive-or-ing (XOR-ing) each corresponding bit within the message with the key portion being used. For reasons of efficiency, the actual exclusive-or operation may be performed in batches of 32 bits as a single operation. The message is therefore encrypted a corresponding number of times. Decryption could occur using the same key used to encrypt, by re-XOR-ing the relevant portions of the key. However this would not decrypt using a relative's DNA sequence, which would generally contain common portions without being identical.

Such decryption may be achieved as follows. In one embodiment, the decrypter creates their key in the same way as the encrypter, except that the decrypter uses their own sequenced DNA to create the ProDNA and therefore the key. The decrypter does not have access to the encrypter's DNA nor know what the encrypter's sequence is. The decrypter decrypts each segment, XOR-ing the relevant portion of the key. Where there are portions of DNA shared by both parties, those portions will decrypt correctly. Where they are not, those bit values will, on average, have a 50:50 chance of being correct or wrong.

Where the same bit is encrypted across many segments, and the encrypter and decrypter share half of their DNA, and the bit being encrypted is 1, it is expected that the following values will result:
- 50%=typical percent of the time it is stored as a 0 in the crypt.
- 50%=typical percent of the time it is stored as a 1 in the crypt.
- 0%=percent of the time it XOR decrypts back to 0 where both sender and receiver share the corresponding bit in their sequenced DNA.
- 100%=percent of the time it XOR decrypts back to 1 where both sender and receiver share the corresponding bit in their sequenced DNA.
- 50%=percent of the time it XOR decrypts back to 0 where both sender and receiver do not share the corresponding bit in their sequenced DNA.
- <50%=overall percent of time it XOR decrypts back to 0.
- >50%=overall percent of time it XOR decrypts back to 1.

Decryption may be achieved by voting bit by bit, and then testing the outcome against the check value as described below. There may be several calibration factors which can serve to increase or decrease a likelihood of a successful decryption and hence the detection of how closely related the individuals need to be for success. These may be set as a proportion of the volume setting.

Large centralised sequenced queues can be difficult to maintain. However, in at least one embodiment any sequenced queues generated through the chromosomal identification arrangement do not need to be centralised. The messages just need routing to the correct destination. TCP/IP packet switching has already shown that such issues can be solved globally. The sequenced queues are used for routing, and hence one or more algorithms can be used to route using the queues.

The chromosomal identification arrangement enables a distributed database of messages 656 to be held across a distributed network of nodes, including a DNA address. The DNA address is the sender's address, but also sender and receiver either share a fragment of their respective DNA addresses, or a respective portion of their DNA addresses comprise one or more numbers which are of a predetermined closeness to each other. Each node sends each message it receives classically to one or more other nodes. The node sends the message to the nodes that, according to the data known, have messages coming from or going to those address fragments. This distributed processing technique leads to close relatives' messages meeting each other, converging and hence reaching the same nodes.

This process is performed by going through the 12 Σ values from the table 105 in the address that the message is coming from and/or going to. In each of those 12 cases the previous message is located that had the same number in the same place, or, if one is not found, the two nearest matches optionally comprising the number above and the number below. In one embodiment this could provide up to 24 other messages. That list is then expanded to take into account the other messages that have been associated as part of the potential families of those up to 24 messages. Several of these messages and potential families may have been double counted, and hence subsequently be reduced to a single count. The message the node is attempting to forward will then be forwarded to all of the internet addresses that were associated with those messages after the internet addresses themselves have been reduced to the single count.

The DNA address may comprise one addition significant number. Given the 12 numbers already mentioned it is possible for two individuals within the same family to have all 12 numbers disclosed herein comprising identical values. This thirteenth number is used to dis-ambiguate family members from each other and may be represented as a hash of their entire genome. However, this still carries a risk of mixing up identical siblings. Where there is considered such a risk to be avoided of there being identical siblings, an additional sequence creation time stamp can be superimposed upon the hash.

An individual's own node is the only node that is allowed access to the individual's genome sequence. This is used to create their DNA address, encrypt messages they send and attempt to decrypt messages they receive.

A superposition address problem can arise where two unrelated individuals may appear to be related, as a side effect of using address routing information which cannot be used to reverse engineer the individual's genome. The encryption mechanism ensures only related individuals will be able to read each other's messages. Therefore, the chromosomal identification arrangement seeks to address the risk of imposters and DNA superposition by checking whether decryption was successful to determine whether the individuals are indeed related. Where relatedness is thus established, individuals are then connected into family units, as when persons A & B are both related to person C, then persons A & B are also related to each other. Failure to decrypt can be judged as indicative of either an imposter or a case of DNA address superposition.

The chromosomal identification arrangement may be arranged to include a "volume" mechanism. As the volume measure is increased, the further afield genetic relations will be accepted as related.

In order to message family members, it may be necessary to send (or "route") a message from an individual to an address of one or more of their family members, wherein only the sender's genome sequence is known. Central to the address are several descriptive numbers. Addresses are relevant relative to each other. The distance between any two addresses can be calculated. The descriptive numbers are indexed, in such a way that close values can also easily be obtained.

Each node of the chromosomal identification arrangement is operable to send messages to the nearest known relatives, thereby causing clusters to occur.

Two distinct forms of encryption may be used:
1) Verbatim 140—using any of the mitochondria 115, or the X 120 or Y 125 chromosomes.
   Based on shared and non-publicly disclosed cryptographic keys, the verbatim cryptographic key 140 takes advantage of the fact that these three chromosomes can be passed from parent to offspring, with certain provisos, verbatim.
2) Unique 150—using chromosome numbers 1 through to 22 as shown in item 155.
   These chromosomes together, with rare exceptions such as in the case of identical siblings, are conventionally accepted as being unique to each individual. Encryption is performed using the chromosomes which tend to be unique to each individual but taking into account the fact that portions of the abovementioned chromosomes may be shared with relatives or even just with other human beings. The proportion shared may be indicative of the biological closeness between two individuals. Decryption requires a voting scheme, taking account of that fact that more than 50% of the key available for decryption may be "broken" from a cryptographer's perspective. In conventional cryptography, a recipient of a code relies on having an entire and correct key in order to decrypt. In this context, because the key for encryption and a different key for decryption are taken from different people who only share part of their DNA, the non-shared portions can be considered as broken or simply white noise from a decryption point of view.

A verification check may then be performed taking advantage of the fact that decryption is even possible. Unless the key, comprising data from the genetic material of the sender, is shared to a predetermined degree of similarity, there can be no decryption. Hence a successful decryption is indicative of a predetermined degree of biological familial closeness. A check digit mechanism or "check value" may be appended to a message and so used to perform such a determination. This reduces the coincidence of repeated parts of the message coinciding with the potential of any repeated parts of the key. In the example of a key with two (pressed) or four (unpressed) bits per base pair, common base pairs would often coincide with common characters. Therefore should the character set use a non-prime number of bits, such as eight, the problem may be overcome through the use of a blob of prime-number sized words (BoPSW) 652 as further detailed below.

When determining the predetermined degree of biological familial closeness, the closest relatives by one definition will share an identical copy of either mitochondria 115, an X chromosome 120, and/or a Y chromosome 125. For these cases encryption and decryption is achieved via shared secret cryptography 112, 150, 102' or "verbatim key cryptography" 140, 140' as described herein where the keys are derived from mitochondria 115, X or Y chromosomes 120, 125 as described above. In cases where people may be related but not as closely or there are sequencing errors or sequencing uncertainty, the keys are derived from chromosomes 1 to 22, 155, wherein the encrypted message 202 comprises multiple copies of the message, encrypted with different parts of the key. The crypt assembly used may be referred to as a crypt bunch 605. A plurality of messages 208 may be included from a selection of family members within a single message 202. Decryption is repeatedly attempted, and a voting mechanism 165 is used to determine which value each bit should have. Where there is not a complete copy of a chromosome allowing shared secret cryptography, there is a need to encrypt and decrypt where sender and related receiver have a key each, portions of which they share, portions of which they do not, and they do not know which portions are which. This is the "unique key cryptography" or "voting cryptography" as further described herein. The key may be generated by:
- digitising the sender's sequences DNA;
- classically formatting it in unpressed form, however other forms could also be used;
- superimposing via XOR operations various chromosomes;
- folding the chromosomes back onto themselves optionally using XOR; and/or
- through various other mathematical operations.

Generating an index sorted by genetic DNA address and accepting the closest available, thereby using one or more distributed processing achieves can significantly reduce the time taken to find a relative when compared with conventional methods of searching. However, it is possible that some individuals do not wish to be found, and hence may only be found where they choose to use the chromosomal identification arrangement, even if the actual system providers are different entities. Nearest relatives using the chromosomal identification arrangement can therefore be connected. Non-users will not be connected, and so can remain hidden from their relatives using the arrangement.

There may be provided one or more calibration tools, operable to adjust how far afield matches can occur. This can be reduced to provide greater ease of use into a single metric referred to as "volume". The "loudest" volume, which can be set to a maximum value of 100, may be described as a broadcast where more distant biological relations can be detected. Volume 1 may represent more of a "whisper" such that only very close relatives will be found. A calculation may be applied to the DNA addresses of two different people, which renders an integer representing the shortest possible genetic distance between the two individuals in terms of base-pairs. A user may additionally wish to "mute" communications from any other individuals with a high volume so as to avoid being disturbed by messages they are not interested in receiving.

Figure 5:
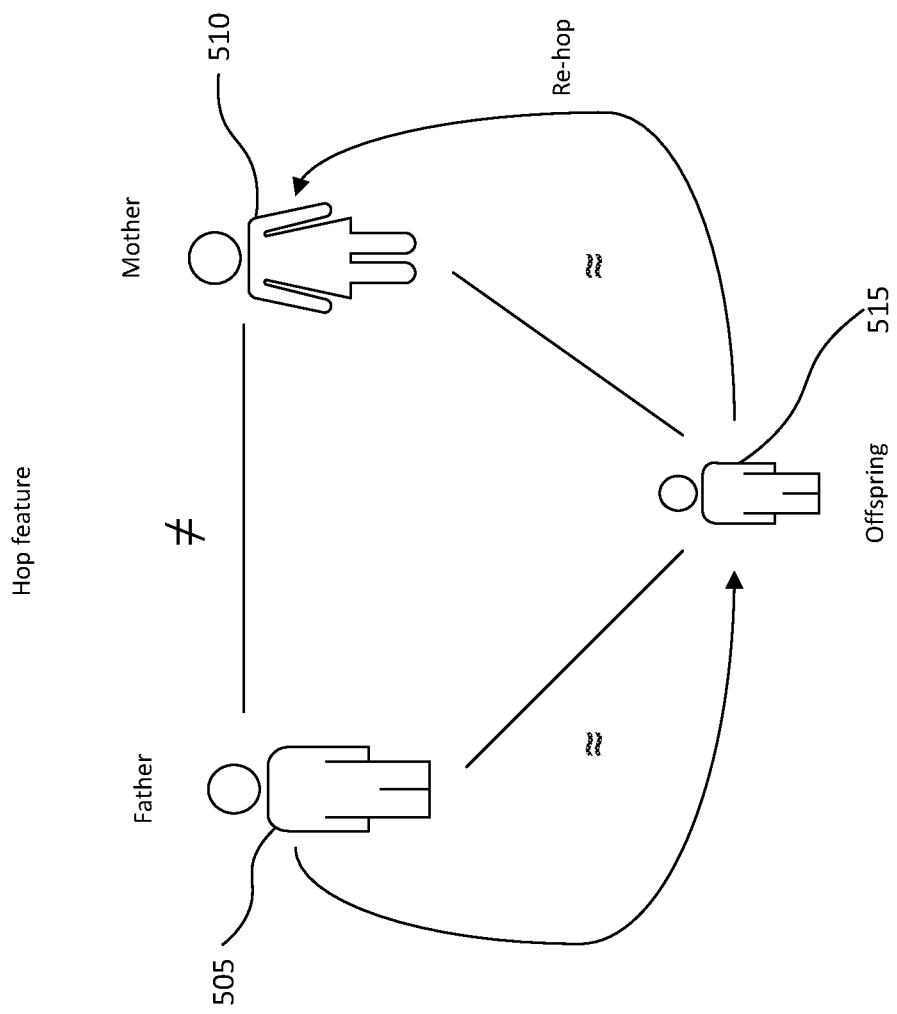
FIG. 5 shows a multi-hop operation.

As shown in FIG. 5, it is observed that some legal or indirect relations, such as a husband 505 and wife 510, may not share a significant proportion of DNA but may still wish to be reconnected. In this example, the husband 505 may be referred to as the father, and correspondingly the wife 510 may be referred to as the mother. Such users may still find each other using the chromosomal identification arrangement, provided there is an intermediary, such as their joint biological offspring 515, using the arrangement. The offspring, being biologically related to each user, can act as a bridge linking those two users together despite their lack of biological similarity. Unlike each of their relationships with their offspring, the husband 505 and wife 510 do not share a blood line with each other. A DNA familial connection with each other is required for two users to be directly linked as being related.

Each node, when decrypting a message, can act as a relay thereby re-encrypting the message using their own intermediated key. This can be a "multi-hop" operation, thereby increasing the breadth of a search. The resulting convergence of messages the routing mechanism disclosed herein allows nodes to put potential families together. Where A is related to B and B is related to C, that means A is related to C. If node B successfully translates a message from A, it may be operable to resend the message and this time enabling C to decrypt and hence view the message. This re-transmission is issued under a fresh message number but includes the original version. This can result in a plurality of differing encrypted crypts of the same message, allowing various attempts to decrypt at any given receiving node.

While an individual's genetic DNA address is derived from an individual's genome sequence, by design it is not possible to reverse engineer their genome sequence from their address. The genome sequence is thereby kept secret. Although encryption and decryption may use an individual's genome sequence, the sequence itself is not transmitted and thus remains secret.

Testing every searching person against every other searching person can generate an unfeasibly large number of searches to achieve. If the Earth's population is 7,600,000,000, this would require comparing 7,600,000,000 DNA tests against 7,600,000,000 other DNA tests, totalling 57,760,000,000,000,000,000 comparisons. Indeed, given the length of time required to complete a conventional DNA test, people may be being added to the list more quickly than they can be tested. This is overcome, in this context, by using a generic DNA address to significantly reduce options and further by using cryptography, as messages will only by decryptable when they are truly related. Moreover, the chromosomal identification arrangement may be arranged to take advantage of distributed processing, as each user can have their own node with their own DNA sequence. These nodes may comprise, for example, a mobile smartphone. Other means of implementation may comprise one or more of: a mobile smartphone application ("app"); a server supporting the aforementioned mobile smartphone app; a PC or laptop version of the mobile smartphone app; a software library for building mobile smartphone apps, servers supporting mobile smartphone apps and/or PC and/or laptop version of the mobile smartphone app; any other networked devices; a text, email or voice mail service wherein the number or address is derived from the user's own DNA profile; and/or a transmission service, where medical information may be of interest to specific families. A wired network connection, such as may be found in a home server 204 as opposed to a mobile smartphone, may provide the advantage of a more consistent signal or connection to an external network such as the internet, as well as a holding bay/storage for incoming messages while a mobile smartphone may be out of range or disconnected from the external network. Additionally, a hash of a home server containing an IP address could serve to distinguish between identical twins as each twin would likely have a different IP address.

In one embodiment, encryption is performed through the use of a blob of prime-number sized words (BoPSW). A "blob" conventionally refers to a Binary Large Object. Messages to be encrypted are placed into a BoPSW. A BoPSW holds characters or words, of a specified size in bits, which is a prime number. This enables a range of character codes to be mapped into a standard form, without introducing the cryptographic weakness of coinciding data and key words. It is understood that this example is illustrative of partial decryption, and such decryption may be performed on a on a bit by bit basis rather than character by character. Computers typically have word sizes of 8, 16, 32 or 64 bits. ASCII, initially defined in seven bits but usually used in 8-bit form, tends to be too limited for international purposes. Unicode, with its 16 bits, may be considered to provide greater internationalisation than ASCII. There are also other character sets, for example those specifically designed for Chinese or Japanese characters. It is a target of the arrangement disclosed herein to not exclude locale options, while remaining cryptographically sound. One-to-one character mappings are not conventionally considered cryptographically sound, even when accidently introduced. The risk of accidental introduction is reduced when the word sizes of data and key do not coincide. BoPSW holds messages in characters which are unlikely to coincide with the natural alignments of DNA. Potential word sizes used by BoPSW are all prime numbers, for example; 7, 11, 13, 17, 19, 23, 29, and 31. It is appreciated that larger prime numbers could be used instead of or in addition to those examples given.

Figure 6A:
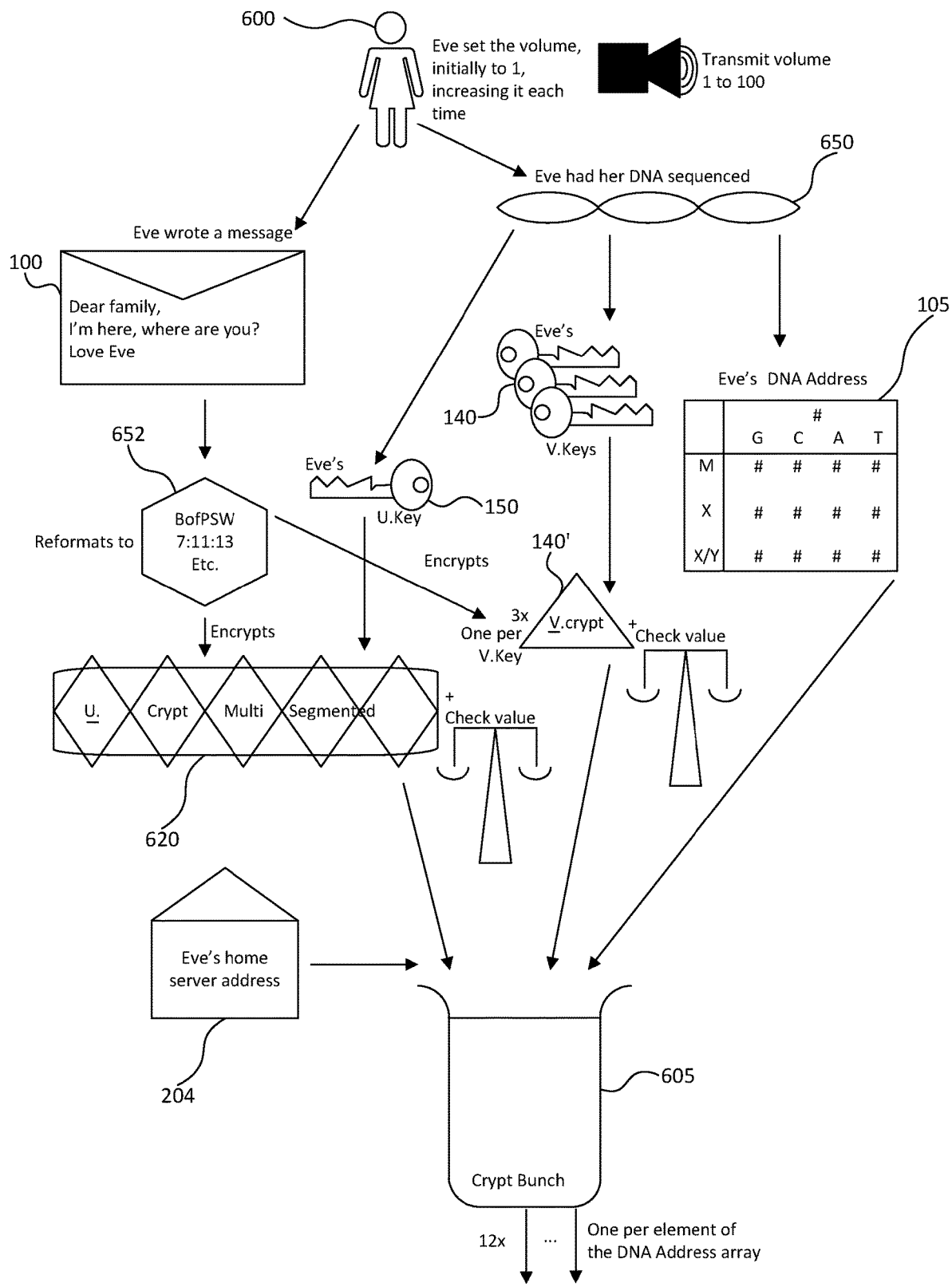
FIGS. 6a, 6b, and 6c show an exemplary embodiment of the arrangement as disclosed herein.
Figure 6B:
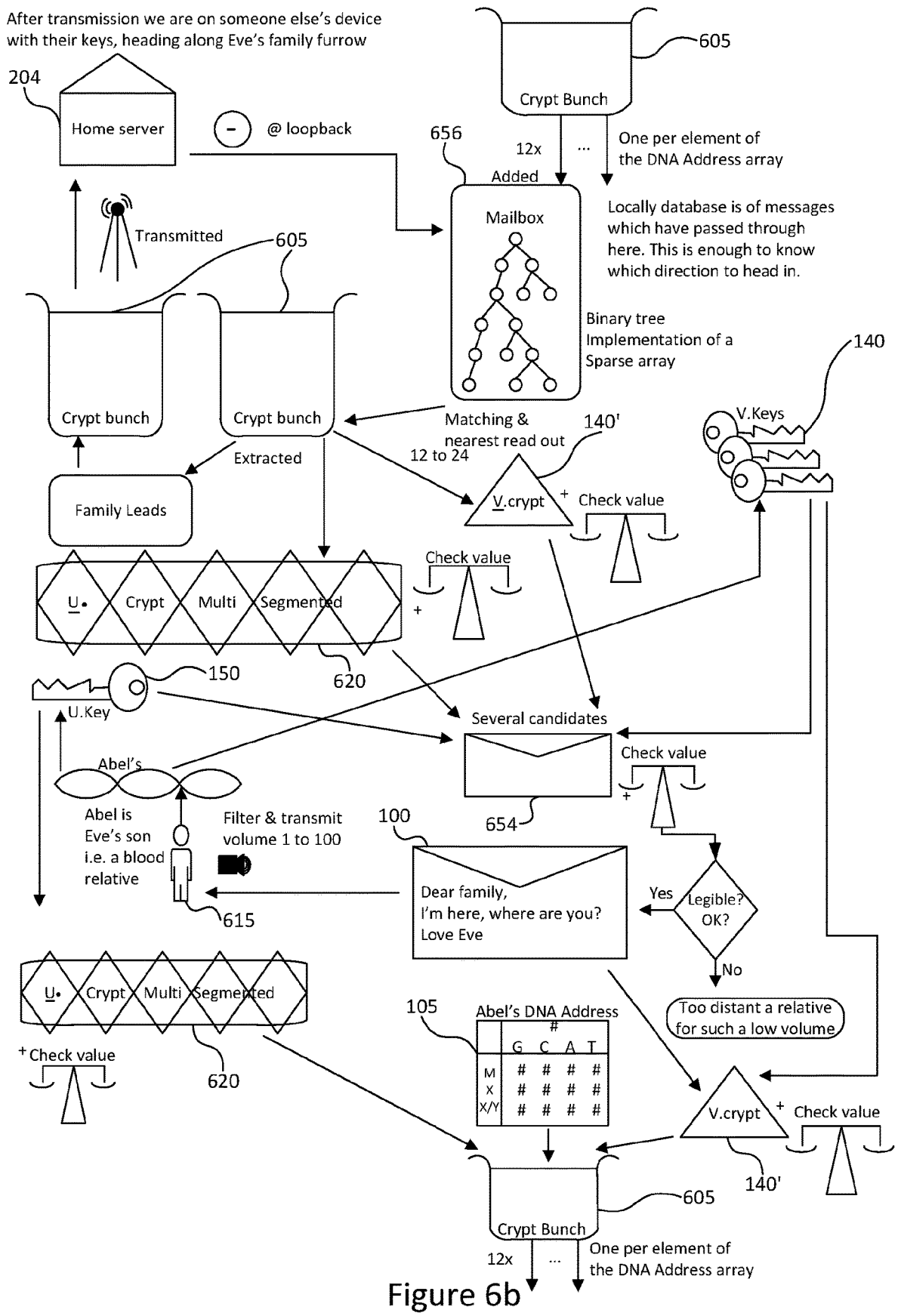
Figure 6C:
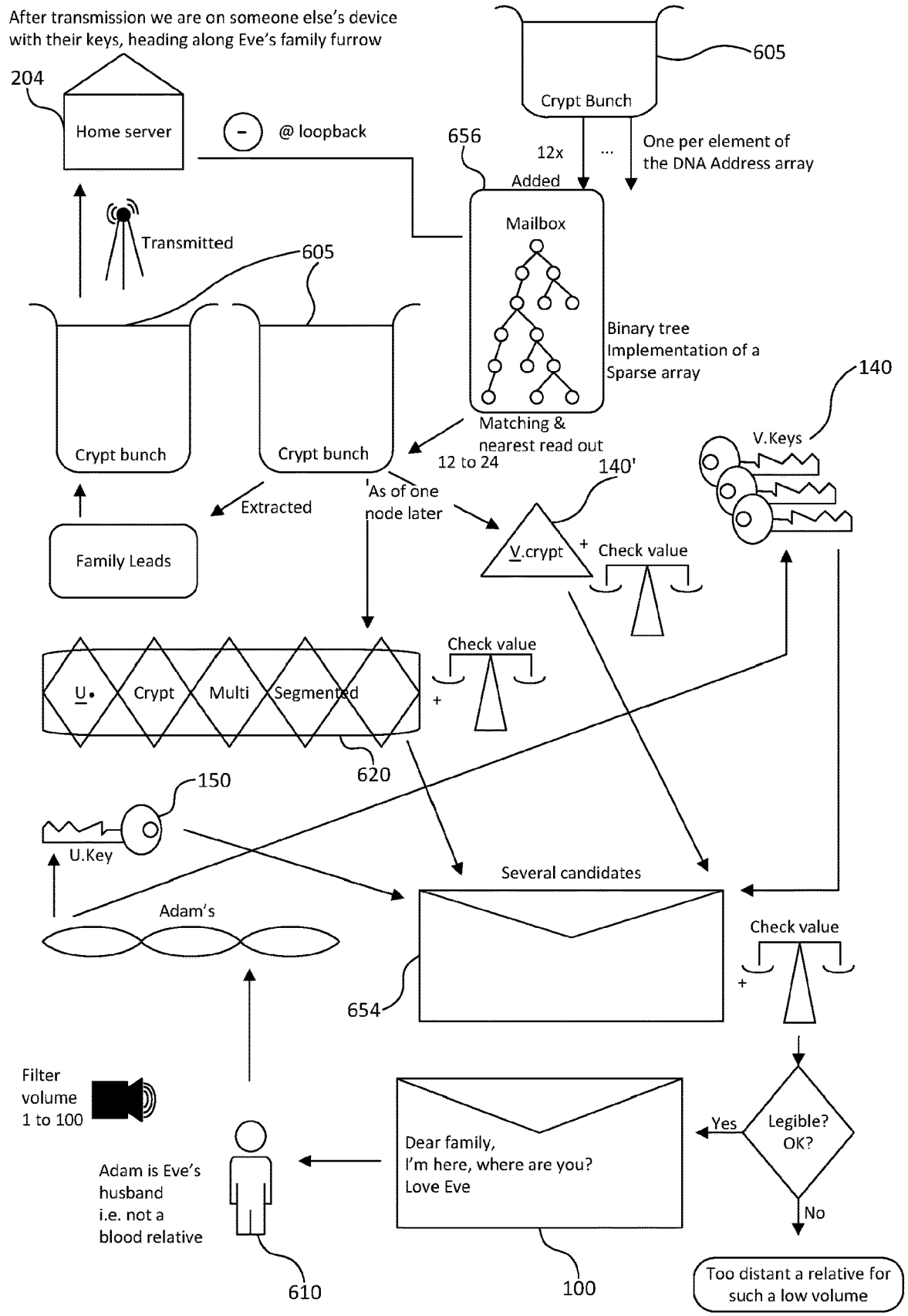

FIGS. 6*a*, 6*b*, and 6*c* show one particular embodiment for a nominal user "Eve" 600, her husband "Adam" 610, and her son "Abel" 615. Adam is not a blood relative to Eve. Eve's DNA is sequenced 650, and the DNA address can be represented as above summarised in the table 105:

|  | # | | | |
|---|---|---|---|---|
|  | G | C | A | T |
| M | # | # | # | # |
| X | # | # | # | # |
| X/Y | # | # | # | # |

In the above table, the following references are made:
"M" refers to the individual's Mitochondria chromosome;
"X" refers to the of one of the individual's X chromosomes;
"X/Y" refers to the other X chromosome in the case of a female, or the Y chromosome in the case of a male;
"G" refers to GC base pairs;
"C" refers to CG base pairs;
"A" refers to AT base pairs; and
"T" refers to TA base pairs.

It is noted above that biological females generally have two X chromosomes, whereas biological males generally only have one.

Each "#" symbol represents a number. Other than the # in the uppermost row, each # is calculated by counting the number of instances of the base pair to which it refers within the corresponding sequenced chromosome. As above, the number calculated is then multiplied by a confidence factor, also referred to as a certainty factor, which in this embodiment is 12.

Sometimes there is a degree of uncertainty as to which base pair is correct. Where such uncertainty is present, for example because there are multiple potential candidates 654, a calculation is performed whereby the number of potential candidates is multiplied by a number as follows:

| Potential Candidates | Multiply by |
|---|---|
| 1 | 12 |
| 2 | 6 |
| 3 | 4 |
| 4 | 3 |

Where there are multiple candidates, each candidate should have the confidence factor applied. As a result, each base pair in the sequence will result in an overall increase of a factor of twelve.

These # values are then subsequently used to route messages toward their destination.

The # in the uppermost row of the table above represents a hash code of the entire genome sequence of the individual. Optionally, where there is a risk of identical siblings, an epoch timestamp representing the sequencing date and time may also be included as part of this hash code.

The following features of the hashing algorithm of this uppermost # may comprise:
a hash of the entire sequenced chromosome;
consistency across all implementations; and
compliance with the classical principles of hash values.

This uppermost # value is used in this embodiment to distinguish the sender from other senders. Any of the other values may be shared by other individuals. Under some circumstances all twelve of the # values may be identical.

Special action may be taken if the node is so fresh that it has no data or knowledge of any other messages having passed through the node. Under such circumstances it passes the message upstream to a pre-defined gateway, which will be able to carry out the processing as outlined below.

Twelve threads each take one of the twelve # values. Each thread compares its # value to the last time it detected a message with an address with the same number on the same place in the address table. If there were none, which may be the case, it uses the nearest number above and also the nearest number below, as though they were a match. The encrypted DNA addressed message will then be forwarded toward the address previously known to have knowledge of that number. Where multiple threads would attempt to send to the same other node, the transmission only occurs once.

Each node that receives the message will carry out the same forwarding process, although loop-backs are prevented. This mechanism drives DNA address element specific furrows across the global network of associated compliant nodes. Where furrows cross, biological relations may be re-connected. Each DNA address has twelve levels it is heading toward. The twelve is made up of three sets of four and classically all four within any given set will match in the same four sets of nodes. The other two sets will be unlikely to match in the same nodes, as they will be reaching out toward a different branch of the family.

Each node will attempt to decrypt in order to discover whether the message is intended for the node's owner. FIGS. 6a, 6b, and 6c illustrate the passage of the message all the way to the recipient.

Referring first to FIG. 6a, an example user "Eve" 600 sets the volume to a low value, aiming to identify only very close relatives—i.e. those with very similar DNA—starting with a volume of 1 out of a maximum value of 100 in this embodiment. Each time Eve uses the system, she can for example increase the volume to increase the range of/audience reached by her message.

Eve has had her DNA sequenced and has this DNA sequence data 650. Eve has also written a message 100 to transmit to any close relatives "Dear family, I'm here, where are you? Love Eve".

As discussed in the embodiments described herein, the message is reformatted to a blob of prime-number sized words (BoPSW) 652.

Using Eve's DNA sequence data 650, a U key 150 is created as well as several V keys 140 and a DNA address for Eve 105.

The U key 150 and the BoPSW 652 are used to encrypt the message using the U key 150 while the V Keys 140 are used to create several encrypted versions of the BoPSW 652. Check values are created alongside the encrypted U Crypt Multi-Segmented message 620 and also against the V Crypt 140' that contained the multiple encrypted versions of the message 100 that are encrypted with each of the V Keys 140.

Eve's home computer address (or home server, or potentially even a remote server under her control) 204 is added along with the U Crypt Multi-Segmented message 620 (and check value) and V Crypt 140' (and check value) and DNA address 105 into a crypt bunch 605.

The crypt bunch 605 can then be transmitted in 12 separate portions, one per element of the DNA address array.

Referring now to FIG. 6b, another user receives Eve's crypt bunch 605 and either forwards or attempts to read the message within or both.

If the crypt bunch is forwarded, it can be addressed based on previous traffic that has passed through the node in order to determine which other node to send the crypt bunch to and/or routing to one or more other nodes using Eve's DNA address 105.

To read Eve's message, Abel uses their DNA sequence 615, from which a U-key 150 and V-Keys 140/v-vault 140', and DNA address 105 have been created. Using these keys, several candidates 654 for the decrypted message are created (along with a check value) and these are determined to be legible or not. If legible, then the message 100 can be shown to Abel but if not legible, then Eve is not a close enough relative based on the volume of her message for Abel to be able to read her message 100. If Abel's volume settings for receipt of messages is set at a threshold lower than Eve's volume, however, then Abel will not be presented with Eve's message 100 regardless of it being legible.

Based on the decryption process at Abel's node, Eve's message 100 may be forwarded on to another node as per FIG. 6c which will now be referred to, but re-encoded using Abel's DNA-derived keys 140,160 and DNA address 105 in order to re-transmit to other family members as per Eve's volume settings—which in this case apply, but where the volume settings don't apply then the process of re-transmission won't occur.

In FIG. 6c, Adam receives Eve's message encoded with Abel's keys as a crypt bunch 605 and repeats the process of attempting to decrypt the message 100 from Eve using Adam's own v-keys 140 and u-key 150 to decrypt Abel's encryption. In this case Adam is for example Eve's husband so not a blood relative to Eve, but is a blood relative of Abel so will be able to decrypt Eve's message via Abel as per Eve's volume settings.

In each case, messages can be relayed back to Eve that someone has decrypted her message.

In an alternative embodiment, there is provided a secure messaging arrangement. The messaging arrangement is operable to use one or more of the encryption and/or decryption techniques described in relation to one or more of the other embodiments. For example, encryption and decryption keys may be generated for a user and shared as appropriate in order to allow other users to securely message that user. Similarly, multiple users can share as appropriate such keys so as to enable bidirectional or multidirectional communication.

In a further alternative embodiment, there is provided a method of verification of identity. The method of verification comprises the use of one or more of the encryption and/or decryption techniques described in relation to one or more of the other embodiments, and can be combined with the use of one or more other identity verification and/or biometric techniques.

Any system feature as described herein may also be provided as a method feature, and vice versa. As used herein, means plus function features may be expressed alternatively in terms of their corresponding structure.

Any feature in one aspect may be applied to other aspects, in any appropriate combination. In particular, method aspects may be applied to system aspects, and vice versa. Furthermore, any, some and/or all features in one aspect can be applied to any, some and/or all features in any other aspect, in any appropriate combination.

It should also be appreciated that particular combinations of the various features described and defined in any aspects can be implemented and/or supplied and/or used independently.

The invention claimed is:

1. A computer implemented method of locating one or more members of a familial network, comprising the steps of:
   generating one or more encryption keys derived from a first genomic sequence;
   encrypting a message using the or each encryption key to form an encrypted message;

sending the encrypted message to one or more remote devices wherein decrypting the encrypted message at the one or more remote devices uses one or more encryption keys derived from a second genomic sequence; and receiving a confirmation regarding whether the decryption of the encrypted message was successful by any of the one or more remote devices wherein, sending the encrypted message comprises generating a genetic address from the first genomic sequence.

2. The method of claim 1, further comprising the steps of:
receiving an input comprising a first genomic sequence; and
generating one or more encryption keys based on the input.

3. The method of claim 1, wherein the step of decrypting the encrypted message at the one or more remote devices uses one or more encryption keys derived from one or more further genomic sequences.

4. The method of claim 1, wherein one or more of the encryption keys comprises:
a first encryption key for a verbatim encryption algorithm, and
a second encryption key for a unique encryption algorithm.

5. The method of claim 4, wherein the first encryption key is used in relation to:
one or more mitochondria;
a first X chromosome; and
a second X chromosome or a Y chromosome,
to form three verbatim algorithmically generated ciphers in relation to the first genomic sequence.

6. The method of claim 4, wherein the second encryption key is used to encrypt the message using a combination of chromosomes 1 through 22 comprised in the first genomic sequence.

7. The method of claim 1, wherein the step of sending the encrypted message is performed using one or more outputs derived from the first genomic sequence.

8. The method of claim 1, wherein the successful decryption of the encrypted message is indicative of a predetermined level of familial closeness.

9. The method of claim 1, wherein the first and/or second genomic sequence comprises at least a portion of a genome sequence.

10. The method of claim 1, wherein a genomic sequence comprises four bases comprising one or more of: guanine (G), cytosine (C), adenine (A), thymine (T), and/or uracil (U); wherein the four bases are mapped to a binary sequence; and wherein the binary sequence comprises two forms: pressed and/or unpressed.

11. The method of claim 1, wherein the input comprises the number of one or more of the four bases.

12. The method of claim 1, wherein the decryption of the encrypted message is successful only if a predetermined proportion of the first genomic sequence corresponds to the second genomic sequence; wherein the predetermined proportion reflects the level of familial relationship between an owner of the first genomic sequence and an owner of the second genomic sequence.

13. The method of claim 1, wherein the step of sending the encrypted message comprises forming an array of three by four integers and a unique individual hashed integer identifier; wherein the unique individual hashed integer is a hash of an entire genome sequence; further comprising a superimposition of a timestamp of the sequencing date.

14. The method of claim 1, wherein the step of encrypting the message comprises the use of a binary large object of prime sized words (BoPSW).

15. The method of claim 1, wherein the or each of the one or more nodes of the distributed network of nodes is only operable to send the encrypted message only the first time that the encrypted message is received by the or each node.

16. The method of claim 1, wherein the or each node of the distributed network has an associated user.

17. The method of claim 1, further comprising the step of:
outputting a measure of genetic distance between the first genomic sequence and the second genomic sequence; wherein the measure of genetic distance is determined using a DNA address.

18. The method of claim 1, wherein the encrypted message is stored for a portion of time on a remote server; wherein the decryption of the encrypted message following the step of sending the encrypted message takes place after a time delay.

19. A familial network location apparatus, comprising:
a hardware processor operable to:
generate one or more encryption keys derived from a first genomic sequence;
encrypt a message using the or each encryption key to form an encrypted message;
send the encrypted message to one or more devices wherein decrypting the encrypted message at the one or more devices uses one or more encryption keys derived from a second genomic sequence; and
receive a confirmation regarding whether the decryption of the encrypted message was successful by any of the one or more remote devices
wherein, sending the encrypted message comprises generating a genetic address from the first genomic sequence.

20. A system to locate one or more members of a familial network, comprising:
a hardware processor operable to:
generate one or more encryption keys derived from a first genomic sequence;
encrypt a message using the or each encryption key to form an encrypted message;
send the encrypted message to one or more devices wherein decrypting the encrypted message at the one or more devices uses one or more encryption keys derived from a second genomic sequence; and
receive a confirmation regarding whether the decryption of the encrypted message was successful by any of the one or more remote devices
wherein, sending the encrypted message comprises generating a genetic address from the first genomic sequence.

* * * * *